United States Patent [19]

Clark, Jr.

[11] Patent Number: 5,871,007
[45] Date of Patent: Feb. 16, 1999

[54] THROAT SPRAY COUNTING MECHANISM

[75] Inventor: Leonard R. Clark, Jr., Oreland, Pa.

[73] Assignee: Chase Marketing International L.L.C., Mamaroneck, N.Y.

[21] Appl. No.: 871,508

[22] Filed: Jun. 9, 1997

[51] Int. Cl.⁶ ................................................. A61M 15/00
[52] U.S. Cl. ............................ 128/200.23; 128/200.14; 128/205.23
[58] Field of Search ................... 128/200.23, 203.15, 128/205.23, 200.14, 203.12

[56] References Cited

U.S. PATENT DOCUMENTS

| | | | |
|---|---|---|---|
| 5,482,030 | 1/1996 | Klein | 128/200.23 |
| 5,549,101 | 8/1996 | Trofast et al. | 128/200.14 |
| 5,740,792 | 4/1998 | Ashley et al. | 128/203.15 |

*Primary Examiner*—John G. Weiss
*Assistant Examiner*—V. Srivastava
*Attorney, Agent, or Firm*—Myron Amer PC

[57] ABSTRACT

An aerosol throat spray with a spray-counting mechanism including a lead screw driven in rotation by a rachet in which a follower on the lead screw moves from a starting location indicating the aerosol is "full" to an ending position indicating the aerosol is "empty", wherein the rachet is actuated by a pawl of springy construction material which, after each power stroke, returns to a ready position for the next power stroke in response to the spring urgency of its construction material.

1 Claim, 1 Drawing Sheet

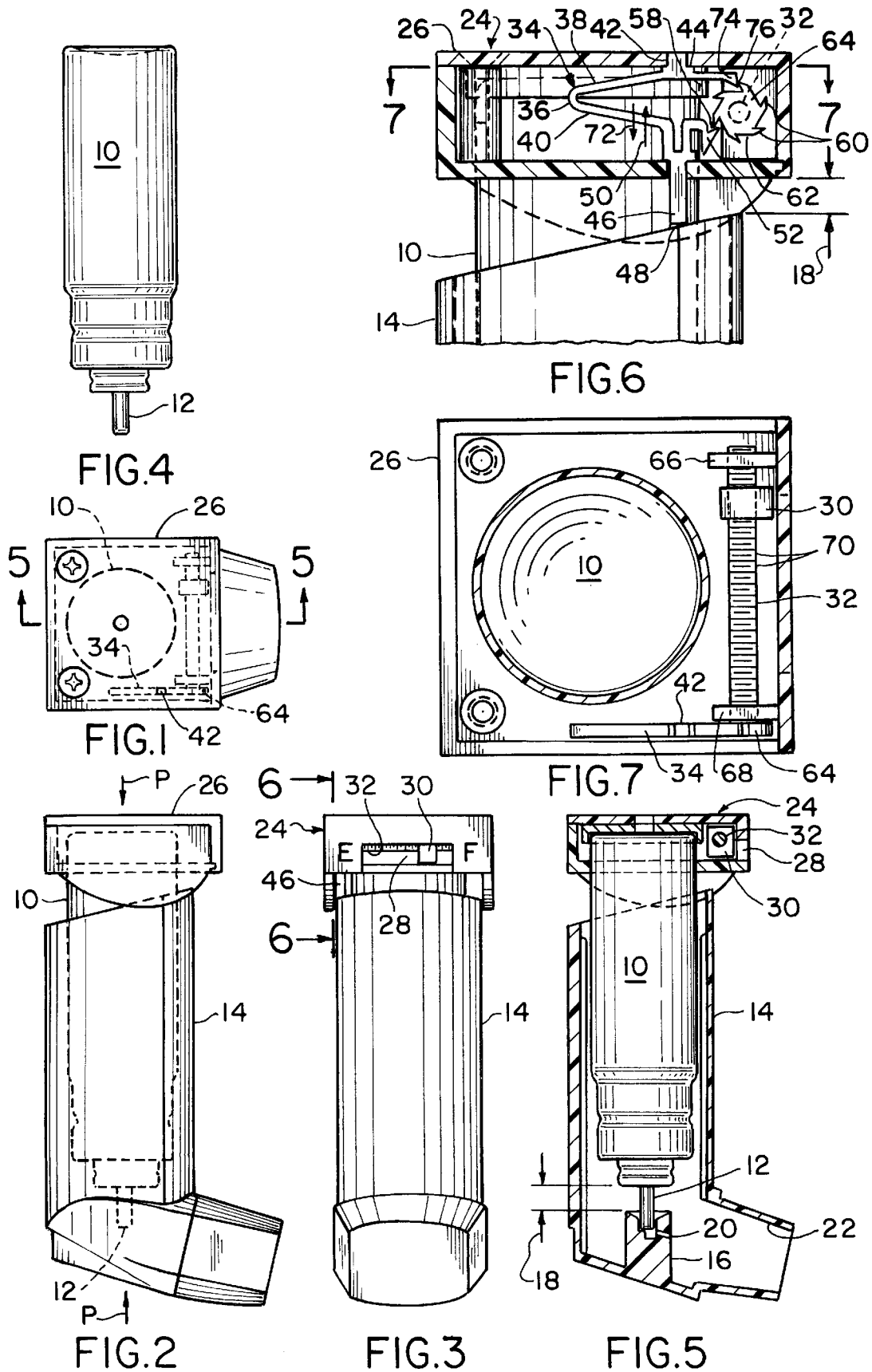

THROAT SPRAY COUNTING MECHANISM

BACKGROUND OF THE INVENTION

The present invention relates generally to a throat spray, and more particularly to improvements in a spray-counting attachment to the spray which in counting the dispensed sprays puts the user on notice when the initially filled aerosol-dispensing medicant container is approaching empty.

EXAMPLE OF THE PRIOR ART

Aerosol sprays with counting mechanisms are already known, one known "Aerosol and Non-Aerosol Spray Counter" being described and illustrated in U.S. Pat. No. 5,482,030 issued to David Klein on Jan. 9, 1996. These known spray counters use a rachet to rotate, during each dispensed spray, a lead screw having a follower thereon, and the position of movement assumed by the follower on the lead screw is one of incremental advances from one end location, signifying "full", to an opposite end location, signifying "empty".

BRIEF SUMMARY OF THE INVENTION

Broadly, it is an object of the present invention to use a greatly simplified rachet-operated counting mechanism for a throat spray overcoming shortcomings of the prior art.

More particularly, it is an object to achieve construction and operating mode simplification for the counting mechanism rachet component by using a combination spring and pawl which operatively drives the rachet in rotation and returns under spring urgency to repeat this operation, to thereby count each dispensed spray as a function of each operation repeated, all as will be better understood as the description proceeds.

BRIEF DESCRIPTION OF THE INVENTION

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a plan view of an aerosol throat spray with a spray-counting mechanism according to the present invention;

FIG. 2 is a side elevational view;

FIG. 3 is a front elevational view;

FIG. 4 is an isolated view of the aerosol throat spray container;

FIG. 5 is a cross sectional view of the mechanism of FIG. 1, but with the mouthpiece cover removed, as taken along line 5—5 of FIG. 1;

FIG. 6 is a partial cross sectional view as taken along line 6—6 of FIG. 3, showing on an enlarged scale details of the within inventive spray counting mechanism; and FIG. 7 is a cross sectional view as taken along line 7—7 of FIG. 6.

DETAILED DESCRIPTION OF THE INVENTION

It is already well known that there is consumer acceptance of an aerosol throat spray associated with a counting mechanism/per spray so that the user is on notice of the once filled aerosol approaching empty, one such combination aerosol throat spray and counter being described and illustrated in U.S. Pat. No. 5,482,030 for "Aerosol and Non-Aerosol Spray Counter" issued to David Klein on Jan. 9, 1996. The Patented counting mechanism uses a rachet type rotating means 54 which could have operatively associated with a shaft 56 thereof, a lead screw/follower combination that will display the follower during its linear movement along the longitudinal axis of the lead screw in a position of movement between end positions designated F, for full, and E, for empty.

With significant improvements as will be better understood as the description proceeds, the present invention contemplates the use of a known aerosol throat spray container 10 having a depending outlet valve stem 12 that, for spraying service, is positioned in a lower throat spray housing 14 with the valve stem 12 in a nozzle 16 so that upon the application of a manually applied upper pressure P (FIG. 2) there is ascending movement 18 only of the stem 12 relative to a stationary container 10 causing the pressure within the aerosol container to release a measured medicant spray through the nozzle outlet 20 and the housing mouthpiece 22 into the user's throat. Upon release of the throat spray housing 14, the pressure P in a known operating mode restores the FIGS. 2 and 5 starting positions to the components, and there thus has occurred a single spraying operation which is counted by a counting mechanism, generally designated 24, disposed within a counting mechanism housing 26 having a friction fit on the top of the aerosol container 10 or otherwise appropriately positioned thereon.

As best shown in FIG. 3, the counting mechanism housing 26 includes a display opening 28 through which there is displayed a follower 30 on a rotating lead screw 32 that advances in incremental movements of one screw pitch per lead screw rotation per spray, from a starting position of movement adjacent the display location F, for full, to the opposite display location E, for empty.

The crux of the invention is the construction and operating mode of the counting mechanism 24, the specifics of which will now be described in particular reference to FIGS. 6 and 7. Occupying an interposed operative position between the upper counting mechanism housing 26 and the lower throat spray housing 14 is a pawl 34 having a C-shaped configuration, as at 36, of springy construction material consisting of spaced-apart upper and lower horizontally oriented arms 38 and 40. In vertical alignment with each other and for positioning an operative end of the pawl 34 adjacent an end of the lead screw 32, are two opposite direction-extending extensions integral to the pawl 34, namely a first extension 42 in ascending relation from the upper pawl arm 38 disposed in engaged relation to the counting mechanism housing 26, as at 44, and a second extension 46 in depending relation integral to the lower pawl arm 40 disposed in engaged relation to the throat spray housing 14, as at 48. The manually applied pressure P causes the housing ascending movement 18 noted in FIG. 5 and also in FIG. 6 in relation to the counting mechanism housing 26 held stationary by the user during a spraying service or use of the aerosol container 10, and during such movement 18 the spaced-apart spring arms 40 and 38 are closed in the direction 50. A laterally positioned or extending tooth 52 integral to the pawl lower arm 40 is thus operatively effective in causing succeeding established meshing engagement, as exemplified at 58, with a cooperating tooth, individually and collectively designated 60, of a circumferential arrangement of such teeth spaced apart a selected distance 62 integral to a rachet means 64 that is mounted on an end of the lead screw 32, so that the lead screw 32 journalled for rotation in end supports 66 and 68 of the housing 26 rotates in unison, i.e. rotation of the rachet means 64 one succeeding tooth at a time, drives the lead screw 32 in rotation. The follower 30 is internally threaded to the pitch of the lead screw threads 70 and is threadably engaged thereon so that the follower 30 which is appropriately held against rotation is advanced in a well known manner lengthwise of the lead screw 32. In practice, the lead screw 32 is preferably provided with twenty-seven operative threads between the end bearings or holders 66 and 68, and each pivotal traverse from one tooth 60 to the next adjacent tooth is one/sixth of a rotation, thereby providing six times twenty-seven single spraying operations to signify an aerosol condition of full (F) or empty (E).

Following the closing movement of the pawl arms 40 and 38 and the delivery of a single spray, the release of the lower and/or upper housing, as the case may be, relative to the other housing, allows an urgency in the springy construction material of the pawl 34 to cause an opposite direction opening movement 72 of the pawl arms 40 and 38, and thus an opposite descending movement in the pawl tooth 52 into a position of movement operatively effective to establish a said succeeding meshing engagement, as at 58, with a next-in-line or next encountered rachet tooth 60. A stop tooth 74 slides over an encountered rachet tool 60 assuming a position as at 76, to prevent counterclockwise rotation of the rachet means 64, as might otherwise occur upon release of the pressure P.

While the throat spray counting mechanism herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. Improvements for a throat spray counting mechanism of a type having a spray-counting display operated by a lead screw driven in rotation by a rachet having plural arrangements of a tooth spaced apart from an adjacent tooth in circumferential relation about said rachet, said counting mechanism having an interposed operative position between an upper counting mechanism housing and a lower throat spray housing, said improvements comprising a pawl having a C-shaped configuration of springy construction material consisting of spaced-apart upper and lower horizontally oriented arms, a first extension in ascending relation from said upper pawl arm disposed in engaged relation to said counting mechanism housing, a second extension in depending relation from said lower pawl arm disposed in engaged relation to said throat spray housing, said first and second extensions of said pawl upper and lower arms having a vertical alignment with each other effective to position said pawl in adjacent relation to a lead screw disposed in said counting mechanism housing, a rachet means having plural arrangements of a tooth spaced apart from an adjacent tooth in circumferential relation about said rachet means connected to said lead screw and adapted to drive said lead screw in rotation, said spray housing being adapted to be manually urged in ascending movement in a spraying operation of an aerosol throat spray container operatively disposed in said spray housing wherein said ascending movement is effective in causing corresponding closing movement of said pawl upper and lower arms, and a laterally extending tooth integral to said pawl lower arm operatively effective in causing succeeding established meshing engagement to a rachet tooth to produce with each said pawl closing movement simultaneous rotation of said rachet means and lead screw, whereby an urgency in said springy construction material of said pawl C-shaped configuration after each said closing movement thereof urges opposite opening movement thereof and a said pawl tooth movement into a position to establish a said succeeding meshing engagement with a rachet tooth.

* * * * *